(12) United States Patent
Egermann et al.

(10) Patent No.: US 7,072,809 B2
(45) Date of Patent: Jul. 4, 2006

(54) METHOD FOR MODELLING FLUID DISPLACEMENTS IN A POROUS ENVIRONMENT TAKING INTO ACCOUNT HYSTERESIS EFFECTS

(75) Inventors: Patrick Egermann, Rueil Malmaison (FR); Olga Vizika-Kavvadias, Rueil Malmaison (FR); Laurent Dallet, Paris (FR); François Kalaydjian, Rueil Malmaison (FR); Christophe Requin, Rouen (FR)

(73) Assignees: Gaz de France, Paris Cedex (FR); Institut Francais du Petrole, Rueil Malmaison Cedex (FR)

( * ) Notice: Subject to any disclaimer, the term of this patent is extended or adjusted under 35 U.S.C. 154(b) by 717 days.

(21) Appl. No.: 10/070,537

(22) PCT Filed: Jul. 10, 2001

(86) PCT No.: PCT/FR01/02212

§ 371 (c)(1),
(2), (4) Date: Jun. 18, 2002

(87) PCT Pub. No.: WO02/06794

PCT Pub. Date: Jan. 24, 2002

(65) Prior Publication Data

US 2002/0173915 A1  Nov. 21, 2002

(30) Foreign Application Priority Data

Jul. 17, 2000   (FR) .................................... 00 09368

(51) Int. Cl.
*G06F 17/50* (2006.01)
*G01N 15/08* (2006.01)
(52) U.S. Cl. .................. 703/2; 703/9; 73/38; 702/12
(58) Field of Classification Search .............. 703/2, 703/10, 9; 73/38, 152.07; 702/12
See application file for complete search history.

(56) References Cited

U.S. PATENT DOCUMENTS 4,381,665 A * 5/1983 Levine et al. ................. 73/73

(Continued)

FOREIGN PATENT DOCUMENTS

FR     2772483     6/1999

OTHER PUBLICATIONS

A New Three-Phase Relative Permeability Model For Various Wettability Conditions, Moulu, et al, SPE 56477 XP-001006316 (Society of Petroleum Engineers) Texas, 3-6, Oct. 1999.

(Continued)

Primary Examiner—Thai Phan
(74) Attorney, Agent, or Firm—Antonelli, Terry, Stout and Kraus, LLP.

(57) ABSTRACT

A modelling method having application to petroleum production, soil cleaning, etc. for optimizing faster and more realistically the displacement conditions, in a porous medium wettable by a first fluid (water for example), of a mixture of fluids including this wetting fluid, another, non-wetting fluid (oil for example) and a gas. The method comprises experimental determination of the variation curve of the capillary pressure in the pores as a function of the saturation in the liquid phases, modelling the pores of the porous medium by means of a distribution of capillaries with a fractal distribution by considering, in the case of a three-phase water (wetting fluid)-oil-gas mixture for example, a stratification of the constituents in the pores, with the water in contact with the walls, the gas in the center and the oil forming an intercalary layer, determination, from this capillary pressure curve, of the fractal dimension values corresponding to a series of given values of the saturation in the liquid phase, modelling the hysteresis effects that modify the mobile saturations of the fluids effectively displaced in the sample, that vary during drainage and imbibition cycles.

6 Claims, 5 Drawing Sheets

U.S. PATENT DOCUMENTS

| | | | |
|---|---|---|---|
| 4,893,504 A | * | 1/1990 | O'Meara et al. .......... 73/152.07 |
| 6,021,662 A | * | 2/2000 | Moulu et al. ................... 73/38 |
| 6,185,985 B1 | * | 2/2001 | Fleury et al. ................... 73/38 |
| 2002/0013687 A1 | * | 1/2002 | Ortoleva ....................... 703/10 |

OTHER PUBLICATIONS

Network Modeling As A Tool To Predict Three-Phase Gas Injection In Heterogeneous Wettability Porous Media, Vizika et al, Journal of Petroleum Science & Engineering, 24 (1999) 155-168.

A New Model To Calculate Three-Phase Relative Permeabilities: Application And Validation For A Sandstone, Moulu, et al XP-000831355.

Network Modeling To Predict The Effect of Wettability Heterogeneities on Multiphase Flow, Laroche et al XP-001006315—Society Of Petroleum Engineers, Texas Oct. 3-6, 1999.

* cited by examiner

FIG.1
| | Sg=0 | 0.01 | 0.05 | 0.10 | 0.15 | 0.20 | 0.25 | 0.30 | 0.35 | 0.40 | 0.45 | 0.50 | 0.55 | 0.60 | 0.65 | Sw |
|---|---|---|---|---|---|---|---|---|---|---|---|---|---|---|---|---|
| Displ.1 | 0 | .002 | .014 | .04 | .08 | .13 | .20 | .27 | .36 | .30 | .57 | .69 | | .83 | | 0.40 |
| | | | 0.007 | 0.02 | 0.046 | 0.081 | .117 | .205 | .28 | .46 | .48 | 0.57 | | | | 0.44 |
| Displ.3 | 0 | | 0.004 | 0.011 | 0.025 | 0.042 | 0.087 | 0.14 | 0.22 | 0.39 | 0.40 | | | | | 0.50 |
| | | .0002 | .0017 | .006 | .0145 | 0.032 | 0.06 | .105 | .178 | 0.30 | | | | | | 0.55 |
| | | | 0.0007 | 0.0025 | 0.008 | 0.019 | .037 | 0.070 | 0.11 | 0.25 | | | | | | 0.60 |
| | | | 0.00003 | 0.0012 | .004 | .01 | 0.023 | 0.045 | | | | | | | | 0.65 |
| | | | .0001 | .0006 | | | 0.015 | | | | | | | | | 0.70 |
| Displ.2 | 0 | | | | | | | | | | | | | | | 0.75 |
| | | | | | | | | | | | | | | | | 0.80 |
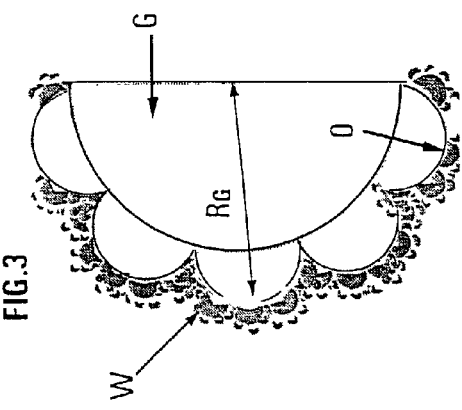
FIG.3
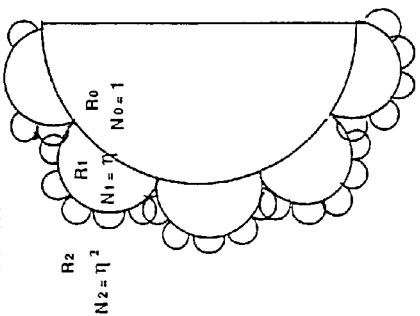
FIG.2

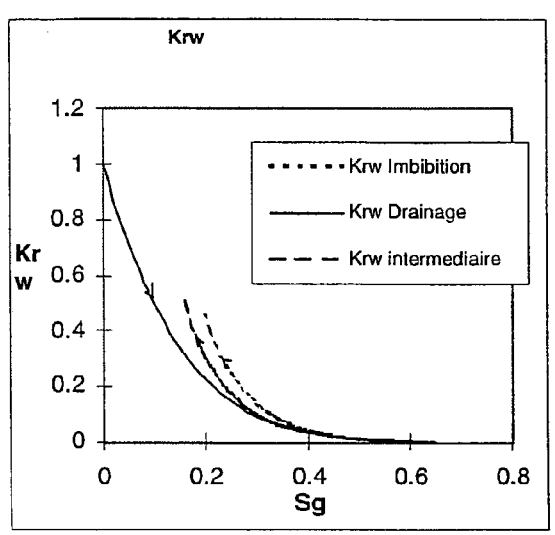
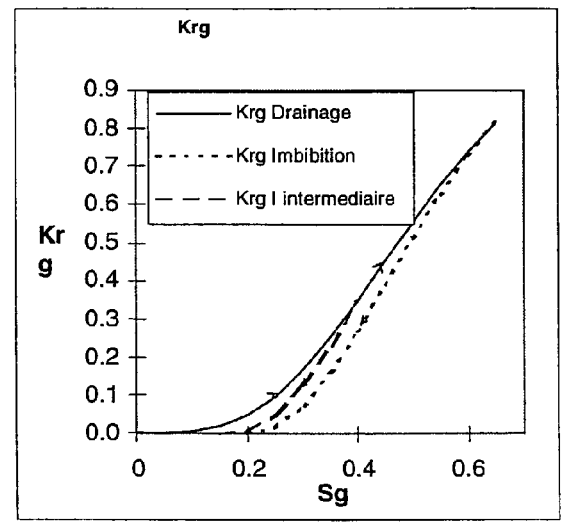
Fig.6A  Fig.6B
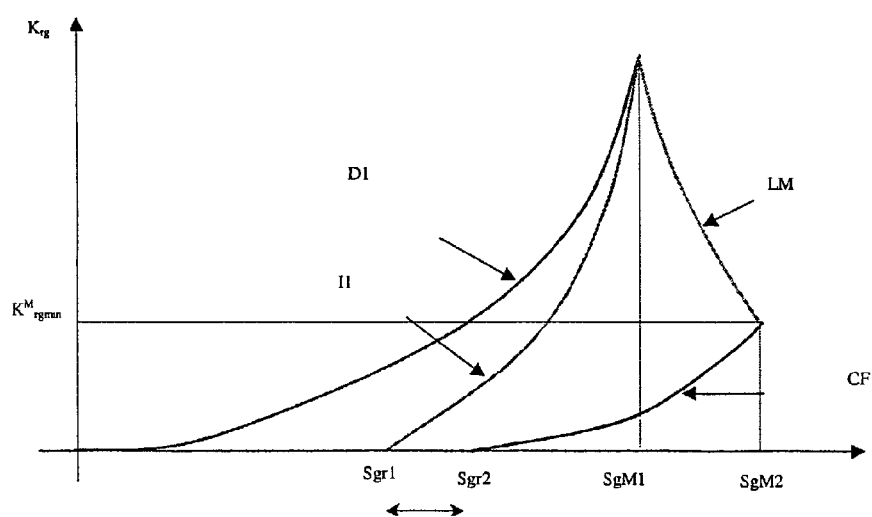
Fig.8

Fig.7
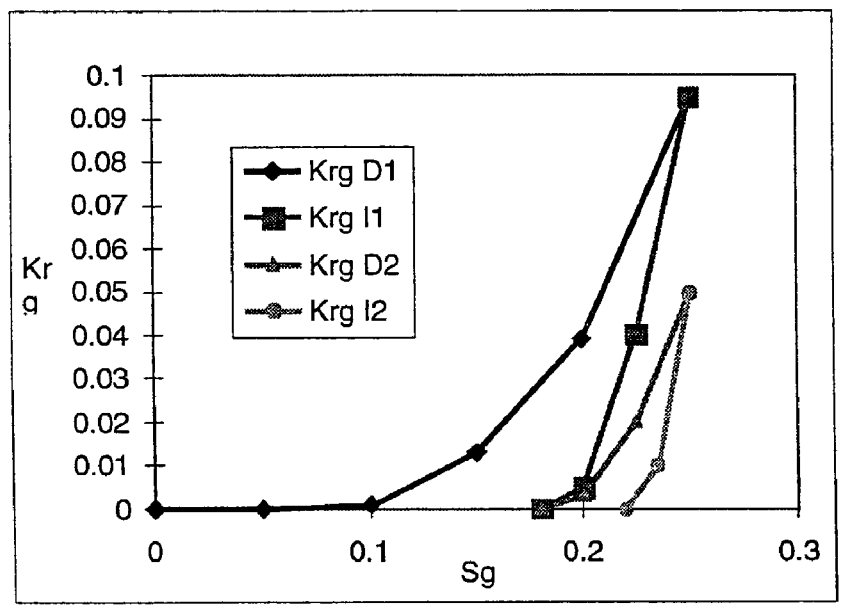
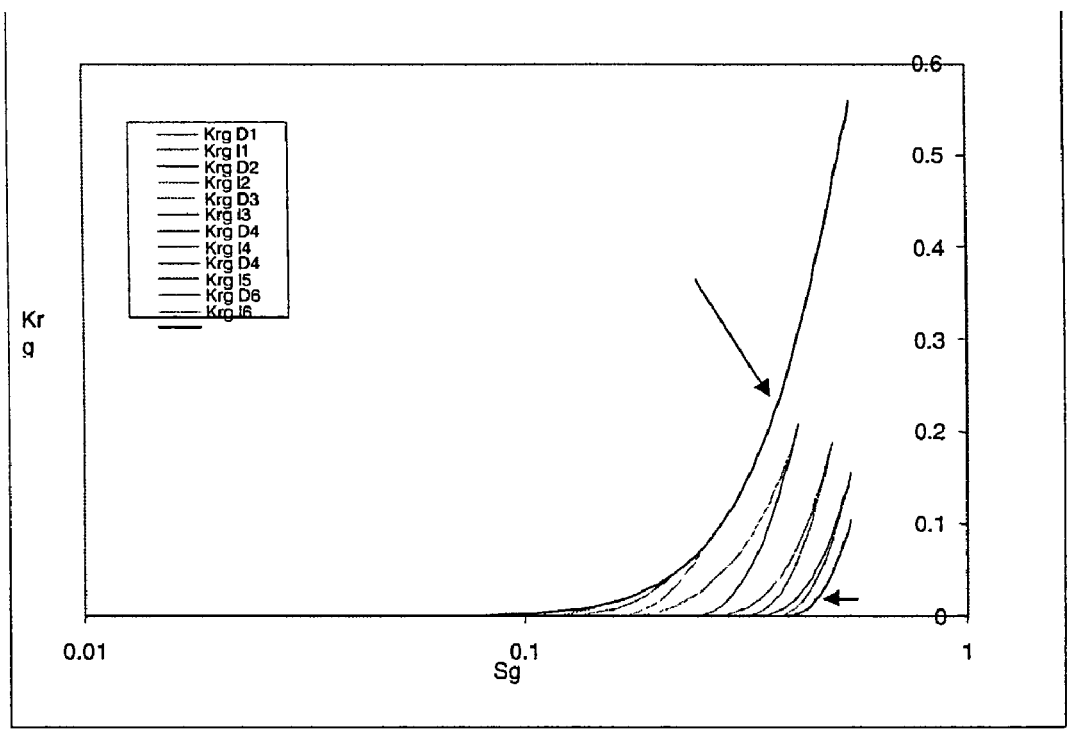
Fig.9

METHOD FOR MODELLING FLUID DISPLACEMENTS IN A POROUS ENVIRONMENT TAKING INTO ACCOUNT HYSTERESIS EFFECTS

BACKGROUND OF THE INVENTION

1. Field of the Invention

The present invention relates to a method for modelling two-phase or three-phase flows in a porous medium, in drainage and imbibition. It is based on a fractal representation of the porous medium and on an original approach for handling phenomena linked with hysteresis (change in the direction of variation of the saturations).

2. Description of the Prior Art

1) Experimental Studies

Experimental determination of the relative permeabilities of a porous medium wherein a multiphase fluid flows is not easy. Measuring operations are usually simplified by considering that one of the phases is immobile in a state of irreducible saturation.

The values are for example acquired by means of a well-known experimental method referred to as "steady state" for determining relative permeabilities, which allows a three-phase fluid to flow with imposed flow rates between the phases. The relative permeabilities expressed as a function of the two saturations are calculated by applying Darcy's law to each phase. It is not an established fact that the relative permeability measurements obtained by means of this method are really representative of the fluid displacements and, in any case, they take a long time because, at each regime change, one has to wait for a state of equilibrium.

Another known method carries out laboratory tests in order to determine measurement tables (as shown in FIG. 1) relating the relative permeabilities and the saturations for each pair of fluids of the three-phase mixture. By adjusting experimental production curves, one tries to progressively adjust the three-phase relative permeabilities. These data tables are then entered into an Athos® type numerical simulator which computes the fluid productions. This method is based on the prior acquisition of many experimental measurements progressively adjusted by calibration and takes a long time.

2) Relative Permeability Models

The known empirical model referred to as Stone's model allows, by empirical correlations, to predict data relative to a three-phase flow from data corresponding to a two-phase flow. It is valid only in case of a high water wettability and it is generally considered to be a poor predictor.

There are two known types of physical models for modelling three-phase flows, based on capillary pressure curves. The capillary pressure curves are connected with a saturation (for example that of the mercury injected) and a pore radius from which the mercury stops for a given injection pressure, determined by Laplace's law, Pinj.

$$Pinj. = \frac{2\sigma}{r}.$$

A first porous media representation model is described by:

Burdine, N. T.: "Relative Permeability Calculations from Pore Size Distribution Data", Trans AIME (1953), Vol. 198, or by Corey, A. T.: "The Interrelation between Oil and Gas Relative Permeabilities", Prod. Monthly (1954), Vol. 19, 38.

According to this model, the porous medium is represented by a bundle of cylindrical capillaries with a radius distribution given by the capillary pressure curve obtained by mercury injection. The permeabilities are obtained by applying Poiseuille's law to the flow of fluids in these capillaries.

This model is based on the representation of the porous medium as an assembly of capillaries with different radii. The relation between the volume and the radius of the pores is given by the value of the slope of the pseudo-plateau. The three fluids are supposed to share the capillaries between them, the wetting fluid (water) occupying the smallest ones, the least wetting fluid (gas) the largest ones and the third fluid (oil) a zone with intermediate-size pores. It is not possible to describe the interactions between the fluids because, in such a model, they flow through separate channels. Finally, this model can be useful only if the pseudo-plateau covers a wide range of saturations. According to this model, the three phases of a three-phase flow move in different capillaries and there is no interaction between them.

Another known physical porous medium representation model is described by:

de Gennes, P. G.: "Partial Filling of a Fractal Structure by a Wetting Fluid", Physics of Disordered Materials 227–241, New York Plenum Pub. Corp. (1985), taken up by Lenormand, R.: "Gravity Assisted Inert Gas Injection: Micromodel Experiments and Model based on Fractal Roughness", The European Oil and Gas Conference Altavilla Milica, Palermo, Sicily (1990).

According to this model, the inner surface of the pores is considered isotropic and has a fractal character, and it can be modelled as a "bunch" of parallel capillary grooves so that the pores exhibit a fractal cross section. The cross section of each pore is constructed according to an iterative process (FIG. 1). The half-perimeter of a circle of radius $R_0$ is divided into $\eta$ parts and each of these $\eta$ parts is replaced by a semi-circle or groove. At each stage k of the process, $N_k$ new semi-circular grooves of radius $R_k$ and of total section $A_k$ are created.

The fractal dimension DL of the cross section at the end of stage k is related to the number of objects $N_k$ generated with the given scale $I_k$ by the relation:

$$N_k \infty I_k^{-DL}$$

The fractal dimension can be deduced from a mercury capillary pressure curve according to the following procedure. Mercury is injected into a porous medium with an injection pressure that increases in stages. Laplace's law allows deducing the pore volume, knowing the volume of mercury injected for a given capillary pressure and the drainage capillary pressure curve relating the injection pressure to the amount of mercury injected and the curve relating the proportion of the total volume occupied by the pores and the size of the pores can be constructed. In cases where a wetting liquid is drained from the porous medium such as water by gas injection, the correlation between the gas-water capillary pressure and the saturation of the wetting phase is given by:

$$P_C = S_W^{\frac{1}{DL-2}}$$

The experimental results readily show that the values of the gas-water relative permeabilities expressed as a function of the three saturations, obtained from the expressions given by the known models and the phase distribution modes in the structure of the pores, are far from the measured values and therefore that the models concerned prove to be too simplistic to represent the complex interactions that take place between the fluid phases.

French Patent 2,772,483 (U.S. Pat. No. 6,021,662) describes a modelling method for optimizing faster and more realistically the flow conditions, in a porous medium wettable by a first fluid (water for example), of a mixture of fluids including this wetting fluid and at least another fluid (oil and possibly gas). This method involves modelling the pores of the porous medium by a distribution of capillaries with a fractal distribution considering, in the case of a three-phase water (wetting fluid)-oil-gas mixture for example, a stratification of the constituents in the pores, with the water in contact with the walls, the gas in the center and the oil forming an intercalary layer. It comprises experimental determination of the variation curve of the capillary pressure in the pores as a function of the saturation in the liquid phases, from which the fractal dimension values corresponding to a series of given values of the saturation in the liquid phase are deduced. It also comprises modelling the relative permeabilities directly in a form of analytic expressions depending on the various fractal dimension values obtained and in accordance with the stratified distribution of the different fluids in the pores. A porous medium simulator is used from these relative permeabilities to determine the optimum conditions of displacement of the fluids in the porous medium.

The hysteresis phenomenon relates to the variations in the petrophysical properties (relative permeabilities, capillary pressure, resistivity index, etc.) observed according to whether measurements are performed during drainage or imbibition (these modes respectively correspond to a saturation increase and decrease of the non-wetting phase). This phenomenon must therefore be taken into account to obtain representative relative permeability values.

The prior art concerning hysteresis effects in two-phase and three-phase media is described for example in the following publications:

Land C. S.: "Calculation of Imbibition Relative Permeability for Two and Three-Phase Flow from Rock Properties", Trans AIME 1968, Vol. 243, 149, Larsen J. A., Skauge A.: "Methodology for Numerical Simulation with Cycle-Dependent Relative Permeability", SPEJ, June 1998, and Carlson F. M.: "Simulation of Relative Permeability Hysteresis to the Non-Wetting Phase", SPE 10157, ATCE, San Antonio, Tex., 4–7 Oct. 1981.

FIG. 6 typically shows the course of the two-phase permeability curves $K_{rw}$ resulting from drainage up to irreducible saturation in wetting fluid (M), then imbibition up to residual saturation in non-wetting fluid (NM). The hysteresis phenomenon occurs at two levels. At equal saturations $S_g$, different numerical values are obtained and the end point reached is an unknown that depends on the cusp point $S_{gM}$ from which the displacement mode is changed. This phenomenon is usually attributed to the trapped non-wetting fluid fraction. At equal saturations, the same quantity of mobile fluid is not obtained, which distorts the flow characteristics.

Practically all the models taking account of hysteresis effects involve Land's semi-empirical relation:

$$\frac{1}{S_{gr}} - \frac{1}{S_{gi}} = C_L \quad (1)$$

where $C_L$ represents Land's constant. This relation relates the initial saturation $S_{gi}$ to the residual saturation $S_{gr}$ in non-wetting fluid, in order to evaluate the saturations in trapped and free non-wetting fluid. Assuming that this relation is valid whatever the saturation, it is applied to determine the intermediate mobile fractions during displacement. In the case of two-phase flows, associating this relation with permeability models provides satisfactory results.

In the case of three-phase flows, the hysteresis of the relative permeabilities $K_{rg}$ takes on a particular form. A displacement hysteresis is experimentally observed, as it is the case with two-phase flows (extent of the direction of variation of the saturations), as well as a cycle hysteresis since the permeabilities depend on the saturation record. In FIG. 7, the relative permeability curves $K_{rg}$ corresponding to a first drainage and imbibition cycle (D1 and I1 respectively) are distinct from the corresponding curves (D2, I2) of a second cycle.

The relative permeability model developped by Larsen et al takes these two forms of hysteresis into account. Starting from an approach combining Stone's model in parallel with Land's formula and Carlson's interpolation method, an approach where only the displacement hysteresis is taken into account, Larsen et al have introduced an empirical reduction factor that is a function of the water saturation, which allows to approximate to the permeability reduction of the gas associated with the cycle hysteresis.

SUMMARY OF THE INVENTION

The modelling method according to the invention allows faster optimizing and more realistically the displacement conditions, in a porous medium wettable by a first fluid, of two-phase or three-phase mixtures including the first wetting fluid and at least a second, non-wetting fluid. It therefore provides operators with a more reliable tool for evaluating notably the best displacement modes of the fluids in the porous medium, in drainage and imbibition. It is based on a fractal representation of the porous medium with modelling of the pores by a distribution of capillaries with a fractal section, considering a stratified distribution of the fluids in the pores, the wetting fluid being distributed in contact with the walls and around the second fluid (or around the other two in case of a three-phase mixture).

The method according to the invention is applicable in many fields where fluid flows in porous media are to be modelled in order to optimize the conditions of the displacement thereof in drainage and imbibition. Examples of fields of application are:

a) development of an oil reservoir and notably enhanced hydrocarbon production by injection of fluids, using for example alternate injections of liquid and gas slugs (a method referred to as WAG). It constitutes an advantageous tool allowing reservoir engineers to study also well productivity and injectivity problems;

b) soil depollution and notably depollution of industrial sites by injection of substances such as surfactants in polluted layers;

c) cleaning of filter cakes by displacement of the substances retained therein;

d) wood drying;

e) optimization of chemical reactions for example by displacement of reaction products in a catalyst mass in order to increase the surfaces of contact, etc.

The method according to the invention is directly applicable by reservoir engineers in order to determine, for example, the most suitable enhanced recovery method to be applied to an underground hydrocarbon reservoir. The method can also serve within the scope of industrial site depollution operations for example.

The method comprises in combination:

experimental determination of the variation curve of the capillary pressure (Pc) in the pores of a sample of this porous medium in the presence of a wetting fluid and of at least one non-wetting fluid (by injection of mercury in a sample placed under vacuum for example);

determination, from this capillary pressure curve, of the fractal dimension values corresponding to a series of given values of the saturation in liquids;

modelling the hysteresis effects that modify the mobile saturations of the fluids effectively displaced as a function of the number of drainage and imbibition cycles undergone by the sample, involving different non-wetting fluid trapping or untrapping constants according to whether a drainage stage or an imbibition stage is carried out;

modelling the relative permeabilities directly in the form of analytic expressions depending on the various fractal dimension values obtained; and entering the relative permeabilities in a porous medium simulator and determining, by means of this simulator, the optimum displacement conditions of the fluids of the mixture in the porous medium.

The method is applied for example for determining displacements of fluid mixtures comprising a first wetting fluid, a second, non-wetting fluid and a gas, considering a stratified distribution of the fluids in the pores, the wetting fluid spreading out in contact with the walls, the gas occupying the center of the pores and the second fluid being distributed in the form of an annular layer in contact with both the gas and the first fluid.

The method can notably be applied for determining, by means of a reservoir simulator, the optimum characteristics of substances added to wetting fluid slugs injected in a formation alternately with gas slugs, in order to displace hydrocarbons in place, or those of a fluid injected into the soil in order to displace polluting substances.

Modelling of phenomena by means of the present method has many advantages. It allows a better correspondence with the results obtained in the laboratory because the physical phenomena are better taken into account. The results of the model are therefore better in case of a scale change for example, for modelling an application in an operation field.

The calculating time is reduced by comparison with the time required when tables are used as in the prior methods. Fractal type modelling can better deal with the hysteresis effects encountered when using WAG type injection processes.

The results of the method can furthermore be perfectly integrated into many reservoir simulators: 3D, heterogeneous, composition simulators, etc.

Exploitation of the results by application softwares is facilitated. It is no longer necessary to perform risky interpolations as it is the rule when working from discrete values of the result tables in order to draw isoperms for example.

BRIEF DESCRIPTION OF THE DRAWINGS

Other features and advantages of the method according to the invention will be clear from reading the description hereafter of a non limitative example, with reference to the accompanying drawings wherein:

FIG. 1 illustrates, in the form of a table, the connections existing for a three-phase mixture between the experimentally obtained relative permeability values of a fluid and the saturations for two of the three fluids;

FIG. 2 is a fractal representation of a pore;

FIG. 3 diagrammatically shows the distribution of the phases of a three-phase fluid in a fractal pore with the wetting fluid W in contact with the wall, the gas phase G spread over the greatest part of the volume of the pore (radius RG), the oil O being a layer between the wetting fluid and the gas;

FIGS. 6a, 6B show the effects of the displacement hysteresis affecting the relative permeabilities of the wetting fluid and of the gas, $K_{rw}$ and $K_{rg}$ respectively;

FIG. 7 shows the combined effects of the displacement and cycle hysteresis observed experimentally on the gas phase;

FIG. 8 shows the key curves used for modelling the untrapping constant;

FIG. 9 shows the result obtained with the model within the scope of a WAG type injection.

DETAILED DESCRIPTION OF THE INVENTION

The method according to the invention allows determination of the three-phase relative permeabilities of porous media by using a fractal type model of the porous medium, on the basis of an approach described by:

Kalaydjian, F. J-M et al.: "Three Phase Flow in Water-wet Porous Media Determination of Gas-oil Relative Permeabilities under Various Spreading conditions", 68th Ann. Tech. Conf. and Exh. of the SPE, Houston, Tex., 1993.

The method according to the invention comprises, as mentioned above, modelling the flow of the phases with distribution of the phases in the fractal structure of each pore. In the case of water and oil flowing in a water wet porous structure, the oil flows into the volume of the pore. In the case of a three-phase flow, there is a stratified distribution, the water, which is the wetting fluid, flows along the walls of the pores, the gas circulates in the volume of the pore and the oil flows between the gas and the water. The saturations are calculated as the relative surface area in a cross section occupied by each of the fluids.

At equilibrium, all the grooves having a radius greater than Rk, which is given by Laplace's law $Pc=2\gamma/R_k$, are occupied by the gas, and the smallest tubes by the two other fluids (water and oil). The wetting fluid saturation is thus expressed as the fraction of the area of the occupied tubes.

Calculation of the fraction of the area of the capillaries occupied by the water for all the radii between $R_k$ and $R_\infty$ leads to the following expression:

$$S_w = \left[\frac{R_k}{R_0}\right]^{2-D_L}$$

and, as $Pc=2\gamma/R_k$, the correlation between the capillary pressure and the saturation of the wetting phase is given by:

$$Pc = S_w^{\frac{1}{D_L-2}}$$

where $S_w$ is the saturation of the wetting phase.

Figure 4:
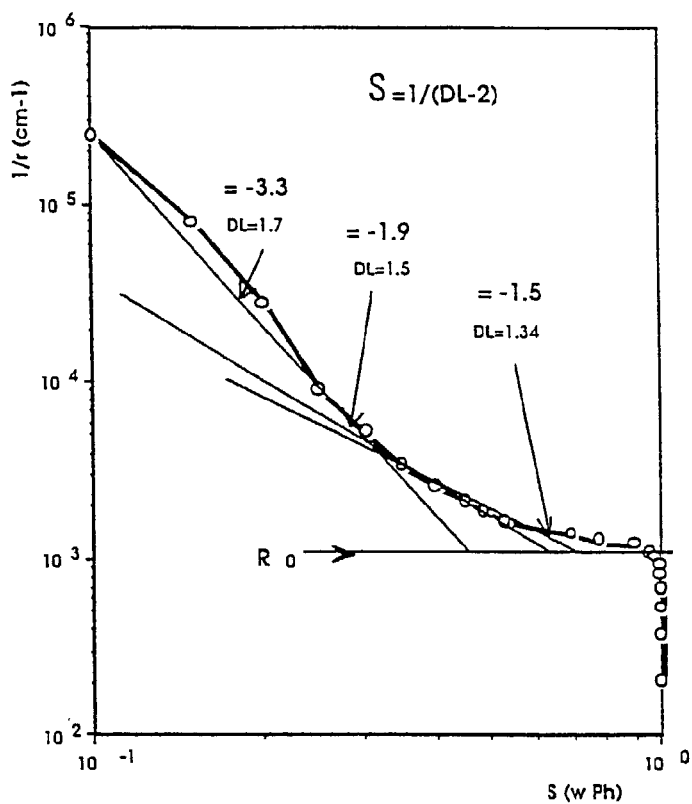
FIG. 4 shows, as a function of the water saturation, the capillary pressure curve of a sample of Vosges sandstone for example, whose local slope S is used to determine the fractal dimension of the pores.

The graphical representation of this correlation in a log—log diagram is a straight line starting from the point $(S_w, P_C)$ corresponding to the largest capillary of the fractal structure with a radius $R_0$. One may suppose that:

radius $R_0$, which is first invaded when mercury is injected (FIG. 4), corresponds to a saturation value of the order of $1/r=10^3$. Each segment of the capillary pressure curve is a part of a line starting from $R_0$ (assumed to be the same for all the different segments), corresponding to the aforementioned correlation $P_C$, $S_w$. Each line has a given slope, a fractal linear dimension can be associated therewith. The values of the slope range from –1.5 to –3.3 as shown in FIG. 4, which leads to values of the fractal linear dimension $D_L$ between 1.3 and 1.7;

each domain is reached by the mercury for saturations corresponding to the place where $R_0$ is found on each line.

The saturation of the two liquids when the gas is present in the pore is calculated as explained above for a phase:

$$S_{Lig} = \left[\frac{R_k}{R_0}\right]^{2-D_L}$$

assuming that the two liquids occupy the tubes whose radii are less than or equal to $R_k$ and the gas, the centre of each pore. The oil saturation is the relative area of the cross section of the grooves occupied by oil, whose radius is less than or equal to $R_k$.

Hysteresis Modelling

Calculation of the relative permeabilities requires determination, for each phase, of the fraction circulating therein and consequently systematic estimation of the saturations corresponding to the stagnant fractions. This must be done for the two cases studied, for example drainage of water and oil by gas, and water imbibition.

The original feature of the modelling procedure accounts for the hysteresis directly at its origin, that is at the level of the non-wetting phase trapping and untrapping phenomena. In FIG. 8, if the curves could be deduced exactly by translation, this would mean that part of the gas has been trapped during the secondary drainage and does not take part in the flow. In fact, this is not the case but the fact that, at equal gas saturation, the permeability is lower during D2 than during I1 means that the trapped gas fraction is larger during drainage. In other words, the non-reversibility of the permeability curves can be explained by a non-reversibility (hysteresis) between the trapping phenomenon and the untrapping phenomenon.

Land's formula (Equation 1) is thus kept, but an untrapping constant, valid during the drainage stages, different from Land's constant valid during the imbibition stages, is introduced. It thus all comes down to modelling the evolution of the untrapping constant during the cycles.

The characteristics to be taken into account in the formulation are as follows. It is considered that $C_P=C_L$ during all the trapping stages because of being directly in Land's conditions of application where a single constant is enough to describe the phenomenon. When $S_{gr}$ is low at the end of the drainage process, $C_D$ is close to $C_P$. This simply means here that the gas is easier to untrap when a small amount thereof is present in the sample, because it can be considered that it is present in large pores that can be readily reconnected during re-injection. When $S_{gr}$ increases, $C_D$ becomes greater than $C_L$, which shows a less efficient untrapping process.

For high gas saturations, a certain reversibility can be encountered, but a trapped gas fraction remains inaccessible in small pores. A low single curve $K_{rg}$ is thus reached, which corresponds to a pseudo two-phase case where the oil is no longer mobile.

According to this representation, based on experimental observations and working hypotheses, the value of $C_D$ passes through a maximum since the untrapping constant is equal to $C_L$ when $S_{gr}$ is low and when it is maximum, when the low-mobility curve is described. The following expression allows reconciliation of all the previous aspects:

$$C_D = \left(\frac{K_{rg}^f - K_{rg\min}}{K_{rg}^{DI}}\right)^E \left(\frac{S_{gt}}{S_{gr2}}\right)(C_{DM} - C_L) + C_L \quad (2)$$

This formulation comprises several parameters:

$C_{DM}$: it takes into account the difference between trapping and untrapping, $C_L$: Land's constant, $K_{rg\ min}$: low-mobility curve, E: calibration parameter, $K^I_{rg}$: value of the relative permeability to gas at the beginning of the previous imbibition, $K^{D1}_{rg}$: value of the relative permeability to gas on the first drainage curve for the gas saturation corresponding to $K^I_{rg}$.

Whatever the order and the nature of the cycle considered, relation (2) and Land's relation (1) allow determination of the trapped and mobile saturations by means of Land's formula while taking into account the three-phase character of the hysteresis (displacement and cycles) without using empirical reduction factors.

$$S_{gf} = \frac{1}{2}\left(S_g - S_{gr} + \sqrt{(S_g - S_{gr})^2 + \frac{4}{C}(S_g - S_{gr})}\right) \quad (3)$$

and $S_g = S_{gt} + S_{gf}$ \quad (4)

C is equal to $C_L$ or $C_D$ according to the displacement mode, $S_{gf}$: free gas saturation, $S_{gt}$: trapped gas saturation.

Calculation of the Relative Permeabilities

A) Relative Permeabilities of Liquids

Figure 5:
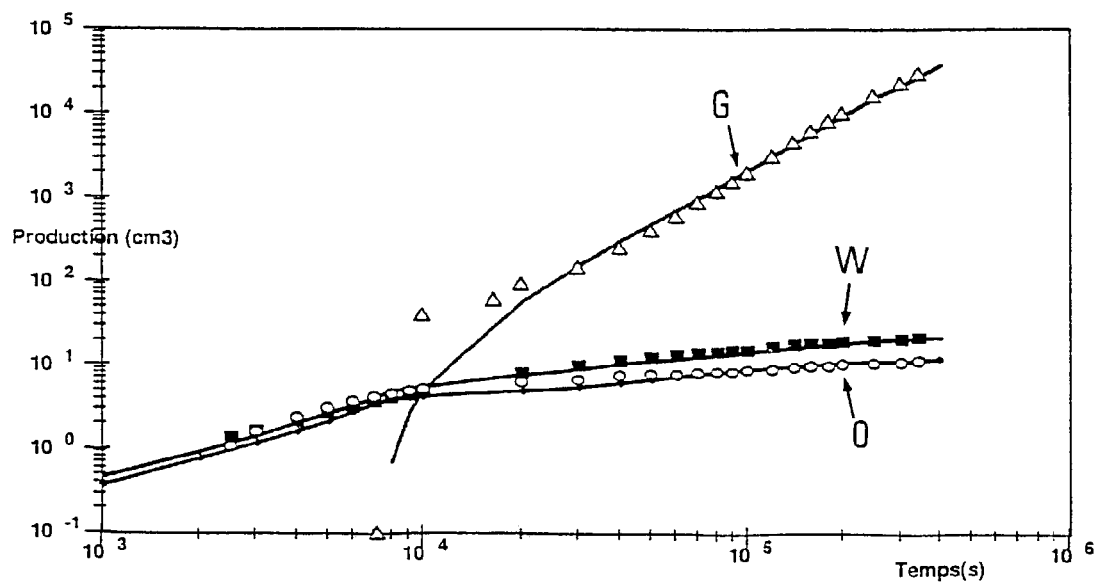
FIG. 5 shows, as a function of time, the production curves obtained experimentally for gas (G), for water (W) and for oil (O), compared with the equivalent curves obtained by simulation by means of the method according to the invention.

Application of Poiseuille's law to each capillary of the bundle for the phase that occupies the capillary allows to calculate the water and oil relative permeabilities (FIG. 5).

Other experimental studies (Larsen et al) have shown that there is a relation allowing to relate the residual oil saturation during the cycles to the trapped gas fraction.

$$S_{or} = (S_{or})_{Sgt=0} - aS_{gt}$$

$(S_{or})_{sgt=0}$ represents the saturation in residual oil left in place in the medium before gas is trapped.

If it is considered only the circulating fraction which contributes to the hydraulic conductivity, the relative permeabilities for water and oil are expressed as follows:

$$K_{ro} = K_{ro}(2Ph)[(S_L+S_{gt})^\beta - (S_w+(1-a)S_{gt}+(S_{or})_{Sgt=0})^\beta]$$

$$K_{rw} = (S_w - R(1-a)S_{gt})^\beta - S_{wi}^\beta$$

R is the reduction factor linked with the trapping of the non-wetting phase.

In these expressions, it is useful to mention that:

the irreducible water saturation $S_{wi}$ is assumed to be stable, the size range of capillaries occupied by the mobile oil is calculated as the difference between the sizes of the capillaries occupied by the two liquids with the total liquid saturation $S_L=S_O+S_W$ and those of the capillaries saturated in water and stagnant oil, $K_{ro}$(2ph.) is the value of the oil relative permeability determined by an imbibition test with water and oil. When only the water and oil phases are present and since the sample tested is water wet, the oil will flow through the section of the pore exactly as the gas in a three-phase flow.

B) Gas Relative Permeability

Since gas is a non-wetting phase, it occupies the central space of the pore and it spreads towards the periphery thereof as the gas saturation increases, however without coming into contact with the solid wall (FIG. 6). It is considered that the gas circulates in a single pore whose radius $R_g$ is given by the relation:

$$R_g = R_0 + R_1 + R_2 + \ldots + R_k,$$

the gas permeability being then given by:

$$K_{rg} = K_{rg\ max}.(1-(S_L+S_{gt})^\alpha)^4 \quad (5)$$

with $$\alpha = \frac{1}{2 - D_L},$$

$D_L$ being the linear fractal dimension of the porous medium and $S_L$ the total liquid saturation equal to $1-S_g$.

The relative permeability model allowing calculating $K_{rw}$, $K_{ro}$ and $K_{rg}$ is installed in a simulator such as ATHOS® or GENESYS©. This allows calibration of experiments carried out in the laboratory and optimizing the conditions to be satisfied in order to displace petroleum fluids in place in a reservoir, either by gas injection or by alternate injection of water and gas slugs (a method referred to as WAG), by taking account of the pressure and temperature conditions prevailing at the production depth.

Validation

Figure 10:
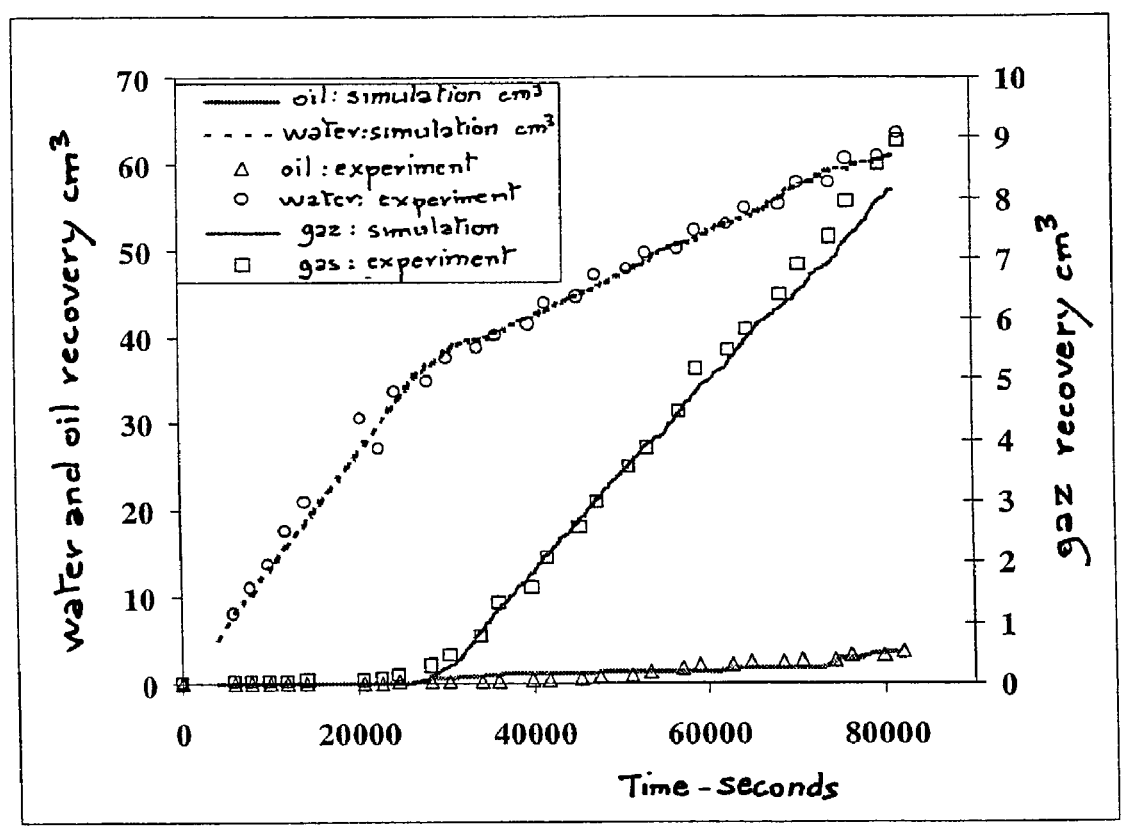
FIG. 10 shows the validation of the model on a WAG type experiment for the recovery curves of the three phases.

The method according to the invention has been validated by means of various types of experiments: gas was injected into porous media containing water and oil, under various conditions. It can be seen in FIG. 5 for example that a very good accordance is obtained between the production curves of the three phases (water, oil, gas) obtained experimentally and those predicted by the reservoir simulator fed with the data obtained in accordance with the method, gas and water were also alternately injected (WAG type injection). FIG. 10 shows that an excellent accordance is also obtained in this case for the three phases throughout the experiment.

The invention claimed is:

1. A modelling method for optimizing displacement conditions, in a porous medium wettable by a first wetting fluid, of a three-phase mixture of fluids including the first wetting fluid and at least a second, non-wetting fluid, comprising:

determining experimentally a variation curve of capillary pressure in pores of a sample of the porous medium in a presence of the first wetting fluid and of the second non-wetting fluid;

modelling the pores of the porous medium by a distribution of capillaries with a fractal section by considering a stratified distribution of the fluids in the pores, the first wetting fluid spreading out in contact with walls of the pores and around at least one other fluid;

determining, from the capillary pressure curve, fractal dimension values corresponding to a series of given values of saturation in liquid phases;

modelling hysteresis effects that modify mobile saturations of the fluids displaced in the sample according to the number of drainage and imbibition cycles undergone by the sample, involving different non-wetting fluid trapping or untrapping constants according to whether the drainage or the imbibition cycles are carried out;

modelling relative permeabilities directly in analytic expressions depending on different fractal dimension values which are obtained; and entering the relative permeabilities into a porous medium simulator and determining, by means of the simulator, optimum displacement conditions for the mixture of fluids in the porous medium.

2. A method as claimed in claim 1, wherein the pores of the porous medium are modelled by a distribution of capillaries with a fractal distribution by considering a stratified distribution of the fluids in the pores, the wetting fluid spreading out in contact with the walls, the gas occupying the center of the pores and the second fluid being distributed in the form of an annular film in contact with both the gas and the first fluid.

3. A method as claimed in claim 2, wherein a reservoir simulator is used to determine optimum characteristics of substances added to wetting fluid slugs injected in a formation alternately with gas slugs in order to displace hydrocarbons in place.

4. A method as claimed in claim 2, comprising using a reservoir simulator to determine optimum characteristics of a fluid injected into soil in order to drain polluting substances.

5. A method as claimed in claim 1, wherein a reservoir simulator is used to determine optimum characteristics of substances added to wetting fluid slugs injected in a formation alternately with gas slugs in order to displace hydrocarbons in place.

6. A method as claimed in claim 1, comprising using a reservoir simulator to determine optimum characteristics of a fluid injected into soil in order to drain polluting substances.

* * * * *